United States Patent
Kadam et al.

(10) Patent No.: US 11,440,882 B2
(45) Date of Patent: Sep. 13, 2022

(54) PROCESS FOR THE PREPARATION OF DEXMETHYL PHENIDATE HYDROCHLORIDE

(71) Applicant: HARMAN FINOCHEM LIMITED, Mumbai (IN)

(72) Inventors: Vijay Trimbak Kadam, Aurangabad (IN); Nareesh Saranapu, Ramachandrapuram (IN); Santosh Uttamrao Chavan, Ahmednagar (IN); Harpreet Singh Minhas, Mumbai (IN); Gurpreet Singh Minhas, Mumbai (IN)

(73) Assignee: HARMAN FINOCHEM LIMITED, Mumbai (IN)

( * ) Notice: Subject to any disclaimer, the term of this patent is extended or adjusted under 35 U.S.C. 154(b) by 174 days.

(21) Appl. No.: 16/319,175

(22) PCT Filed: Jul. 17, 2017

(86) PCT No.: PCT/IN2017/050293
§ 371 (c)(1),
(2) Date: Jan. 18, 2019

(87) PCT Pub. No.: WO2018/015971
PCT Pub. Date: Jan. 25, 2018

(65) Prior Publication Data
US 2021/0371381 A1    Dec. 2, 2021

(30) Foreign Application Priority Data
Jul. 18, 2016 (IN) .............................. 201621024516

(51) Int. Cl.
*C07D 211/34* (2006.01)
(52) U.S. Cl.
CPC ................................ *C07D 211/34* (2013.01)

(58) Field of Classification Search
CPC .................................................... C07D 211/34
See application file for complete search history.

(56) References Cited

U.S. PATENT DOCUMENTS

| 2,507,631 | A |   | 5/1950 | Hartman et al. |
|---|---|---|---|---|
| 2,957,880 | A |   | 10/1960 | Rometsch |
| 5,936,091 | A |   | 8/1999 | Khetani et al. |
| 6,100,401 | A |   | 8/2000 | Prashad et al. |
| 6,162,919 | A |   | 12/2000 | Prashad et al. |
| 6,242,464 | B1 |   | 6/2001 | Harris et al. |
| 2006/0135777 | A1 |   | 6/2006 | Traelet et al. |
| 2011/0130569 | A1 | * | 6/2011 | Prakasam ............... C07B 57/00 546/238 |

FOREIGN PATENT DOCUMENTS

WO    2016/157065 A2    10/2016

OTHER PUBLICATIONS

Renalson, "Efficient Method for Enantioselective Synthesis of Dexmethylphenidate Hydrochloride (FOCALIN)", International Journal of Research and Development in Pharmacy and Life Sciences, Jun.-Jul. 2014, vol. 3, No. 4, pp. 1066-1069.

* cited by examiner

*Primary Examiner* — Timothy R Rozof
(74) *Attorney, Agent, or Firm* — Kramer & Amado, P.C.

(57) ABSTRACT

Disclosed herein a process for the preparation of highly pure dexmethylphenidate hydrochloride (Formula-I) which comprises the steps of neutralization of dl-threomethylphenidate hydrochloride to dl-threo methylphenidate; subsequent resolution of dl-threo methylphenidate using amino acid or its derivatives as chiral resolution agent to yield dexmethylphenidate salt; hydrolysis of the salt and further conversion of dexmethylphenidate into its hydrochloride salt.

15 Claims, No Drawings

PROCESS FOR THE PREPARATION OF DEXMETHYL PHENIDATE HYDROCHLORIDE

FIELD OF INVENTION

The present invention relates to an improved, economically advantageous and industrially applicable process for the preparation of Dexmethylphenidate hydrochloride.

BACKGROUND OF THE INVENTION

Dexmethylphenidate hydrochloride is also known as Methylphenidate hydrochloride, having chemical name as (2R)-phenyl-[(2R)-piperidyl-2-yl]-acetic acid methyl ester hydrochloride.

Methylphenidate hydrochloride exists as two enantiomers i.e. d & l-threo methyl phenidate hydrochlorides and d-threo enantiomer is considered to be active and is available in the market for the treatment of Attention Deficit Hyperactivity Disorder (ADHD).

Several methods are reported for the preparation of dexmethylphenidate hydrochloride by different ways of resolution.

U.S. Pat. Nos. 2,507,631 and 2,957,880 discloses multistep synthesis of methylphenidate (methyl-piperid-2-yl phenyl acetate) wherein, -pyrid-2-yl phenyl acetamide (formed initially by reaction of 2-chloro pyridine and acetonitrile followed by hydration in presence of acid) is catalytically hydrogenated to yield -piperid-2-yl-phenyl acetamide. In U.S. Pat. Nos. 2,507,631 and 2,957,880 -piperid-2-yl phenyl acetamide is separated into threo and erythrodistereomeric racemates through evaporation of solvent; addition of sodium hydroxide to form -piperid-2-yl phenyl acetamide free base and preferential crystallization of the erythro form by passing gaseous HCl in presence of ethanolic solution. The isolated erythroracemate is then resolved through formation of L-tartarate salt which is further subjected to epimerization to yield d-threodiastereomer. Thus according to the procedure disclosed in the said patent, -piperid-2-yl phenyl acetamide is converted to d-threo methyl-piperid-2-yl phenyl acetate through hydrolysis and esterification. However, the process is uneconomical in view of the fact that it involves discarding of threo-piperid-2-yl phenyl acetamideracemate which is isolated following the recrystallization step.

U.S. Pat. No. 5,936,091 discloses a process for resolving piperidylacetamide stereoisomers using dibenzoyl-D-tartaric acid. The d-threo amide derivative thus obtained is further converted to dexmethylphenidate hydrochloride.

U.S. Pat. No. 6,100,401 describes the process for the preparation of d-threo isomer of methylphenidate hydrochloride which comprises resolving the racemic mixture of threo methylphenidate hydrochloride with dibenzoyl-D-tartaric acid to obtain di benzoyl-D-tartrate salt enriched with d-threoisomer of methyl phenidate in a first step, basifying the tartrate salt to obtain the free base form of the d-threoisomer of methylphenidate in a second step, converting the free base into the hydrochloride salt form of the d-threo isomer of methylphenidate in high optical purity in the third step and recrystallizing the hydrochloride salt form to obtain the desired d-threo isomer in a higher optical purity.

U.S. Pat. No. 6,162,919 discloses a process for the preparation of d-threo enantiomer of Methyl phenidate hydrochloride by using (R)-(−)-1,1′-binaphthyl-2,2′-diyl hydrogen phosphate as a resolving agent. The d-threo methyl phenidate hydrochloride (Dexmethylphenidate hydrochloride) obtained from the said process is purified in deionised water to enrich optical purity.

U.S. Pat. No. 6,242,464 discloses a resolution process for single enantiomer d or l-threo methylphenidate which comprises resolution of a mixture of enantiomer using a resolving agent selected from the group consisting of D and L O-O˘ditoluoyl tartaric acid. Ditoluoyl-D-tartrate salt as obtained from the said process is taken for further purification to obtain the product with higher optical purity.

US20060135777 discloses a process for the preparation of d-threo methylphenidate hydrochloride by multistep process comprising the conversion of mixture of threo and erythro enantiomer to give racemic threo amide derivative; resolving the threo amide derivative to its corresponding d-threoenantiomer by using dibenzoyl-D-tartaric acid; acid hydrolysis of d-threo amide derivative using hydrochloric acid to give d-ritalinic acid hydrochloride followed by reaction with thionyl chloride in an inert solvent toluene to give acid chloride of d-ritalinic acid which is further converted to dexmethylphenidate hydrochloride by methanol. Dexmethylphenidate hydrochloride thus obtained by the above method is taken for further purification using deionised water by applying charcoal treatment under hot condition, passing dry hydrogen chloride gas and applying cooling to isolate the pure product of dexmethylphenidate hydrochloride. The yield of the final product obtained with the said process is poor and process is lengthy and tedious which makes the process industrially not applicable.

In view of the above mentioned draw backs of the prior art, such as multi step synthesis, use of expensive resolving agents, there remains a need in the art to provide an industrially viable process for the preparation of dexmethylphenidate hydrochloride in very good yield and purity.

Therefore, the objective of the present invention is to provide a novel, economically feasible and industrially applicable process for the preparation of dexmethylphenidate with high yields and purity. The chiral amino acids used for resolution can be recovered easily which made the process of present invention more economical.

SUMMARY OF THE INVENTION

In line with the above objective, the present invention provides an improved process for the preparation of dexmethylphenidate hydrochloride that overcomes the draw backs of the above mentioned prior arts. The process of the present invention for the preparation of Dexmethylphenidate hydrochloride is industrially applicable, cost effective, eco-friendly and easy to operate.

The process for the preparation of D exmethylphenidate hydrochloride yields better yield and quality as compared to the prior art.

Accordingly, the invention provides a process for the preparation of optically pure dexmethylphenidate hydrochloride of Formula-I,

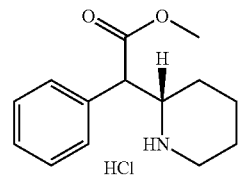

Dexmethylphenidate hydrochloride which comprises the steps of:
(a) neutralizing dl-threo methylphenidate hydrochloride with a base in presence of an ester or aromatic hydrocarbon solvent to obtain dl-threo methylphenidate;
(b) resolving the dl-threo methylphenidate with a suitable chiral amino acids or its derivatives in presence of an alcohol or ketone solvent to obtain amino acid salt of dexmethylphenidate;
(c) converting the dexmethylphenidatesalt obtained in step (a) into its free base in presence of ester solvent or halogenated hydrocarbon solvent; and b) resolving the dl-threo methylphenidate with a suitable chiral amino acids or its derivatives in presence of an alcohol or ketone solvent to obtain amino acid salt of dexmethylphenidate;
c) converting the dexmethylphenidate salt obtained in step (a) into its free base in presence of ester solvent or halogenated hydrocarbon solvent; and
d) converting the dexmethylphenidate obtained in step (b) into its hydrochloride salt.

The process of the present invention is shown in scheme I below.

Scheme I

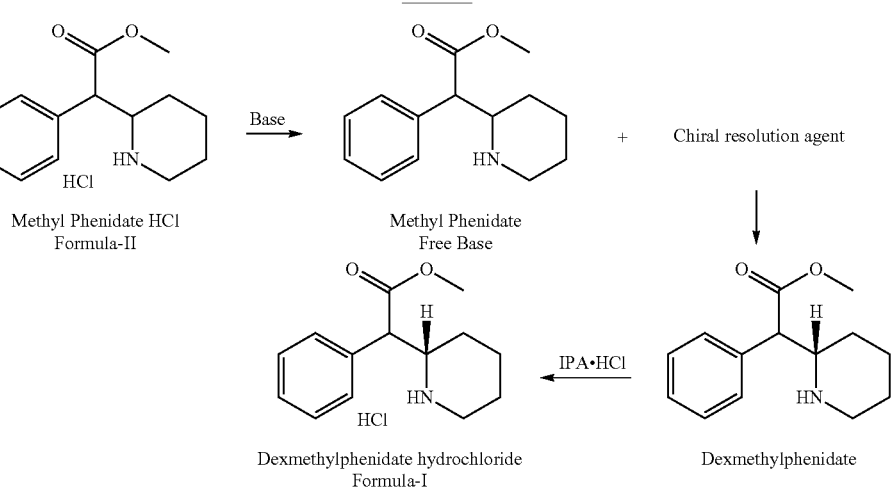

(d) converting the dexmethylphenidate obtained in step (b) into its hydrochloride salt.

The chiral amino acids used in the process for resolution can be recovered easily which made the process of present invention more economical.

DETAILED DESCRIPTION OF THE INVENTION

The invention will now be described in detail in connection with certain preferred and optional embodiments, so that various aspects thereof may be more fully understood and appreciated.

Accordingly, the invention provides a process for the preparation of optically pure dexmethylphenidate hydrochloride of Formula-I, Formula-I

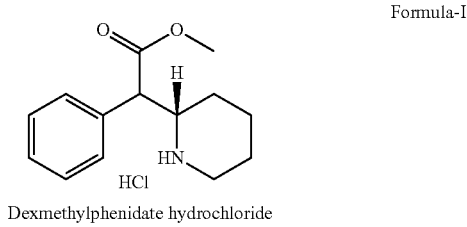 [SMILES: COC(=O)C(c1ccccc1)[C@@H]1CCCCN1 ; Cl]

Dexmethylphenidate hydrochloride which comprises the steps of:
a) neutralizing dl-threo methylphenidate hydrochloride with a base in presence of an ester or aromatic hydrocarbon solvent to obtain dl-threo methylphenidate;

According to the above scheme, in step a) the methylphenidate hydrochloride is neutralized into its free base by treating with aqueous base in presence of a solvent selected from the group consisting of dichloromethane, cyclohexane, heptane, toluene etc. The aqueous base is preferably selected from sodium hydroxide or potassium hydroxide.

According to step b), the Methylphenidate free base thus obtained is treated with a chiral amino acid or its derivatives as resolving agent in presence of an alcohol or ketone solvent to obtain chirally pure dexmethylphenidate amino acid salt.

The chirally pure dexmethylphenidate amino acid salt thus obtained is further hydrolysed using an aqueous base selected from sodium hydroxide or potassium hydroxide to obtain chirally pure dexmethylphenidate, which is further converted to hydrochloride salt by treating with IPA/HCl.

The suitable chiral amino acid or its derivatives are selected from the group consisting of L-methane sulfonyl Valine, N-paratoluenesulfonylV aline, L-acetyl Valine, Leucine, isoleucine, L-phenyl alanine, methanesulfonyl aspartic acid, methanesulfonyl glutamic acid, benzenesulfonyl aspartic acid, benzenesulfonyl glutamic acid, paratoluenesulfonyl aspartic acid, N-paratoluenesulfonyl (tosyl) glutamic acid, paranitrobenzenesulfonyl aspartic acid, paranitrobenzenesulfonyl glutamic acid, parachlorobenzenesulfonyl aspartic acid, parachlorobenzenesulfonyl glutamic acid and the like.

The solvent used for resolving dl-threo methylphenidate is selected from alcohols such as methanol, ethanol, n-propanol, isopropanol and the like, ketones such as acetone, ethyl methyl ketone (MEK), methyl isobutyl ketone (MIBK) or mixtures thereof. The resolution reaction may be conducted at ambient temperature, preferably in the range of 25 to 40éC.

The ester solvent or halogenated hydrocarbon solvent used in the conversion of dexmethylphenidate salt into dexmethylphenidate is selected from the group consisting of ethyl acetate, Ethyl butyrate, Ethyl lactate, Butyl acetate, Isopropyl acetate, Isobutyl acetate, Isoamyl acetate, dichloroethane, dichloromethane, cyclohexane, heptane, toluene etc.

The starting material, methylphenidate hydrochloride is prepared according to the process disclosed in our Indian patent IN 264168 (Scheme II) which comprises:

(a) Hydrolysing-phenyl-pipyridylacetamide (Formula III) in presence of an acid at reflux temperature, followed by treatment with an alkali solution to yield threo-phenyl-pipyridyl-2-acetic acid (formula IV) and (b) Converting threo-phenyl-pipyridyl-2-acetic acid into methylphenidate hydrochloride (Formula II) by reacting with methanol in the presence of an acid catalyst followed by treatment with IPA-HCl.

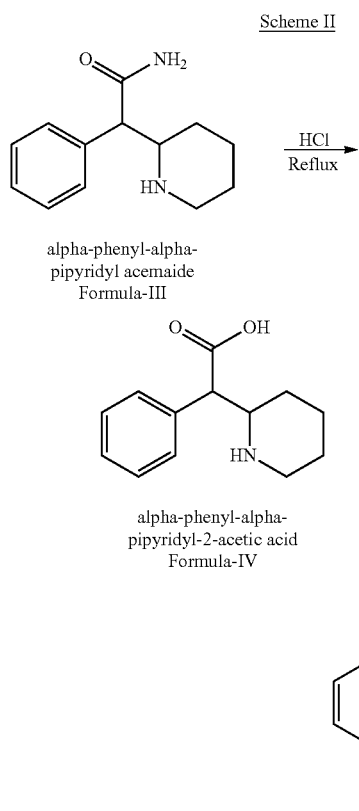

Scheme II alpha-phenyl-alpha-pipyridyl acemaide
Formula-III alpha-phenyl-alpha-pipyridyl-2-acetic acid
Formula-IV Methyl phenidate HCl
Formula-II The process of the present invention yields the dexmethylphenidate hydrochloride with an optical purity of >99.5% and with the yields in the range of >85%.

The above chiral amino acids used for resolution can be recovered easily which made the process of present invention more economical.

The following examples, which include preferred embodiments, will serve to illustrate the practice of this invention, it being understood that the particulars shown are by way of example and for purpose of illustrative discussion of preferred embodiments of the invention.

EXAMPLES

Example-1

Preparation of threo-phenyl-pipyridyl-2-acetic acid

The reactor was charged with a mixture of -phenyl-pipyridyl-2-acetamide (100 g) with 20% aqueous solution of hydrochloric acid (500 ml) and was heated to reflux for 2-6 hrs till completion of the reaction. The reaction mixture was cooled to ambient temperature followed by dilution with water (950 ml) to get clear solution. To the clear solution was added with constant stirring dichloromethane (200 ml) for 30 min, and the layers were separated. Aqueous layer thus obtained was treated with activated carbon, stirred for 30 min and filtered. The pH of the filtrate was adjusted to 6.0-7.0 using aqueous sodium hydroxide solution to yield 88.2 g (88.6%) of threo-phenyl-pipyridyl-2-acetic acid.

(Chromatographic purity by HPLC>99.5%), (Isomeric purity: Threo-99.9%, Erythro 0.10%)

Example-2

Preparation of dl-threomethylphenidate hydrochloride

To a solution of threo-phenyl-pipyridyl-2-acetic acid (75 g) and methanol (750 ml) was added thionyl chloride (83 g) maintaining the temperature below 10éC. The reaction mass was kept under stirring overnight at room temperature. Excess methanol was then distilled off under reduced pressure and the reaction mass was further cooled to 10éC. Purified water (900 ml) was then charged maintaining the temperature between 0-10éC followed by addition of ethyl acetate (375 ml) under constant stirring. pH of the mixture was made alkaline using dilute caustic solution, with stirring followed by separation of the layers. The separated aqueous layer was once again extracted with ethyl acetate (225 ml). The combined ethyl acetate layers were then washed with water and ethyl acetate distilled off completely. To the residue was charged isopropyl alcohol (225 ml) and cooled to 0-5éC. The reaction mass as then acidified by adding hydrochloric acid (25% solution in isopropanol) at 0-10éC. The temperature was raised to 25éC, stirred at this temperature for 2-4 hrs, cooled the reaction mass again to 0-10éC and stirred for 2 hrs. The precipitated solid was filtered off, washed with chilled isopropyl alcohol and air dried to get 82.2 g (89.0%) of dlthreo methyl phenidate hydrochloride. (Chromatographic purity by HPLC: >99.5%)

Example-3

Preparation of dl-threo methylphenidate free base from dl-threomethylPhenidate hydrochloride dl-threomethylphenidate hydrochloride (25.0 gm) was added to 250 ml ethyl acetate at ambient temperature and pH is adjusted with 20% sodium hydroxide solution at 0-5éC. The mixture is then stirred at 20-25éC for about 1-2 hours. Deionized water was added. The organic layer was separated and washed with 10% Sodium Chloride solution followed by drying over sodium sulphate and concentration under vacuum to obtain the desired free base.

Example-4

Preparation of dl-threomethylphenidate from dl-threomethylphenidate hydrochloride dl-threomethylphenidate hydrochloride(25 μm) was added to 20%NaOH solution is diluted with 100 ml water and stirred at room temperature till a uniform suspension is obtained. Cyclohexane was added to the suspension and stirred again for 1-2 hours at room temperature. Separated Cyclohexane the layer and washed with 10% NaCl solution, dried over sodium sulphate and further distilled off under vacuum to yield dl-threo methylphenidate.

Example-5

Preparation of dl-threo methylphenidate from dl-threomethylphenidate hydrochloride dl-threo methylphenidate hydrochloride was stirred in a mixture of MDC and 20% NaOH solution for 1 hour to get clear solution. MDC layer is separated and aqueous layer was back-extracted with MDC. The combined MDC layers were washed with 10% NaCl solution and dried over sodium sulphate. The layer was concentrated under vacuum to get dl-threomethylphenidate.

Example-6

Preparation of dl-threo methylphenidate from dl-threomethylphenidate hydrochloride dl-threomethylphenidate hydrochloride (25 gm) is added to 250 ml Toluene at ambient temperature and pH is made alkaline with 20% sodium hydroxide solution at 0-5éC. The mixture is then stirred at 20-25éC for about 1-2 hours. De-ionized water was added. The organic layer is separated and washed with 10% NaCl solution. The organic layer is dried over sodium sulphate followed by concentration under reduced pressure to obtain dl-threomethylphenidate.

Example-7

Preparation of N-tosyl-l-glutamate Salt of Dexmethylphenidate

To a solution of dl-threo methylphenidate (25 gm) and acetone, there was added N-tosyl-l-gutamic acid and the mixture was heated to ambient temperature. Then the solution was cooled to room temperature. The crystals were collected by filtration and washed with acetone, dried to obtain the N-tosyl-1-glutamate salt of Dexmethylphenidate (25 gm).

Example-8

Preparation of L-tosylglutamate Salt of Dexmethylphenidate

A mixture of 60.9 gm L-tosyl glutamic acid and 76 gm dl-threo methylphenidate in acetone is stirred for 2 hours at ambient temperature. The slurry was filtered and washed with 50 ml acetone. Dried the material to obtain glutamate salt of L-tosyl Dexmethylphenidate as a white solid (79.2 gm).

Example-9

Preparation of N-tosyl-L-glutamate Salt of Dexmethylphenidate

A mixture of dl-threomethylphenidate base (50 gm), N-tosyl-L-glutamic acid (45.2 gm) and acetone(500 ml) is heated at 50éC. After stirring for one hour 50éC, the mixture is slowly cooled to 30éC over a period of 4 hours. Filtered to collect off white crystals of dexmethylphenidate (52 gm).The optical purity of N-tosyl-L-dexmethylphenidatesalt is 99.0%.

Example 10

Preparation of pure Dexmethylphenidate Hydrochloride

N-tosyl-L glutamate salt of dexmethylphenidate obtained from the above examples was dissolved in water and pH is adjusted to about 8.0 to 9.0 with 20%sodium hydroxide. Extracted the product with ethyl acetate, separated the layers and the organic layer was dried over sodium sulphate. Ethyl acetate was distilled off completely under reduced pressure to obtain a residue, charged Isopropyl alcohol (4V) and activated carbon. Filtered to remove carbon, collected the filtrate and slowly added IPA-HCl solution. A white material was precipitated. Stirred for 1 hour at RT and cooled to 5éC and maintained under stirring for 1 hour. Filtered and washed with isopropyl alcohol and dried under vacuum below 70éC to obtain dexmethylphenidate hydrochloride having optical purity 99.7%).

Example 11

Preparation of pure Dexmethylphenidate Hydrochloride

To a mixture of N-tosyl glutamate salt of dexmethylphenidate (12.46 gm), water (150 ml) and MDC (150 ml), added 2N NaOH solution to adjust the pH to ~11.0. Separated the layers, MDC layer was washed with water and the aqueous layer was extracted with MDC. Combined both MDC layers, dried over sodium sulphate and concentrated under reduced pressure to yield crude dexmethylphenidate. The crude dexmethylphenidate was taken in isopropyl alcohol and heated to get clear solution. Cooled to room temperature and stirred for 1 hour, to which slowly added IPA. HCl solution to obtain a white crystalline solid. Filtered the solid and washed with isopropyl alcohol. Dried the product under vacuum below 70éC to obtain pure dexmethylphenidate hydrochloride (6.13 gm) having an optical purity of 99.9%.

Example 12

Preparation of pure Dexmethylphenidate Hydrochloride

To a mixture of N-tosylglutamate salt of dexmethylphenidate (12.46 gm), water (150 ml) and ethyl acetate (150 ml), was added 2N NaOH solution until pH ~11.0. Separated the layers, ethyl acetate layer was washed with water and the aqueous layer was extracted with ethyl acetate. The ethyl acetate layers were combined, dried over sodium sulphate and concentrated under reduced pressure to yield crude dexmethylphenidate. The crude dexmethylphenidate was taken in isopropyl alcohol and heated to get clear solution.

Cooled to room temperature and stirred for 1 hour. Slowly added IPA .HCl solution, a white crystalline solid is observed. Filtered the solid and washed with isopropyl alcohol. Dried under vacuum below 70éC to obtain pure dexmethylphenidate hydrochloride (6.13 gm) having an optical purity of 99.9%.

Example 13

Recovery of N-Tosyl-L-glutamic acid

A solution containing L-methylphenidate-N-tosyl-L-glutamate (Mother liquor obtained after preparation of N-tosyl glutamate salt of dexmethylphenidate) was dissolved in methanol and was concentrated under vacuum and diluted with ethyl acetate. The mixture was warmed to 40éC and 1M sodium hydrogen carbonate solution was added slowly. The mixture was stirred for 30 minutes then the lower aqueous phase containing N-tosyl-L-glutamic acid as its disodium salt was separated off. The organic phase was stirred with water (0.5 liters) at 40éC. for 30 minutes. The lower aqueous phase was separated off. The aqueous phases were combined and 2-butanol (0.5 liters) was added. The mixture was warmed to 40éC. and hydrochloric acid (552 ml) was added slowly. The mixture was cooled to 10éC. and stirred for 30 minutes then the solid N-tosyl-L-glutamic acid was collected by filtration and washed twice with water. The solid was dried at 50éC, HPLC purity of Recovered N-tosyl-L-glutamic acid is 99% and chiral purity is 97-99%.

We claim:
1. A process for the preparation of optically pure dexmethylphenidate hydrochloride of Formula-I,

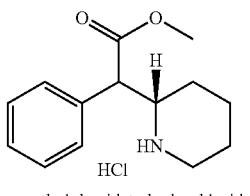

Formula-I

Dexmethylphenidate hydrochloride comprising:
 a) neutralizing dl-threo-methylphenidate hydrochloride with a base in the presence of an organic solvent to produce dl-threo-methylphenidate;
 b) resolving the dl-threo-methylphenidate with a chiral amino acid or a derivative thereof in the presence of an alcohol or ketone solvent to obtain an amino acid salt of dexmethylphenidate, wherein the chiral amino acid is selected from the group consisting of valine, leucine, isoleucine, L-phenylalanine, glutamic acid, aspartic acid, and combinations thereof;
 c) converting the amino acid salt of dexmethylphenidate into its free base in the presence of a base and an organic solvent; and
 d) converting the free base of dexmethylphenidate obtained in step (c) into its hydrochloride salt.

2. The process according to claim 1, wherein the neutralizing step comprises neutralizing dl-threo-methylphenidate hydrochloride with an aqueous base.

3. The process according to claim 2, wherein the neutralizing step comprises neutralizing dl-threo-methylphenidate hydrochloride with aqueous sodium hydroxide or aqueous potassium hydroxide.

4. The process according to claim 1, wherein the neutralizing step comprises neutralizing dl-threo-methylphenidate hydrochloride in the presence of an organic solvent selected from the group consisting of ethyl acetate, dichloroethane, dichloromethane, cyclohexane, heptane, toluene, and a mixture thereof.

5. The process according to claim 1, wherein the neutralizing step comprises neutralizing dl-threo-methylphenidate hydrochloride in the presence of an organic ester solvent or an aromatic hydrocarbon solvent.

6. The process according to claim 1, wherein the neutralizing step comprises neutralizing dl-threo-methylphenidate hydrochloride in the presence of an organic solvent selected from the group consisting of dichloromethane, cyclohexane, heptane, toluene, and a mixture thereof.

7. The process according to claim 1, wherein the resolving step comprises resolving the dl-threo-methylphenidate in the presence of an alcohol or ketone solvent selected from the group consisting of methanol, ethanol, n-propanol, isopropanol, acetone, methyl ethyl ketone (MEK), methyl isobutyl ketone, and a mixture thereof.

8. The process according to claim 1, wherein the step of converting the amino acid salt of dexmethylphenidate into its free base comprises:
 converting the amino acid salt of dexmethylphenidate into its free base in the presence of an organic solvent selected from the group consisting of an ester solvent, a halogenated hydrocarbon solvent, and a mixture thereof.

9. The process according to claim 8, wherein the step of converting the amino acid salt of dexmethylphenidate into its free base comprises:
 converting the amino acid salt of dexmethylphenidate into its free base in the presence of an organic solvent selected from the group consisting of ethyl acetate, ethyl butyrate, ethyl lactate, butyl acetate, isopropyl acetate, isobutyl acetate, isoamyl acetate, dichloroethane, dichloromethane, and a mixture thereof.

10. The process according to claim 1, wherein the step of converting the amino acid salt of dexmethylphenidate into its free base comprises:
 converting the amino acid salt of dexmethylphenidate into its free base in the presence of an organic solvent selected from the group consisting of ethyl acetate, ethyl butyrate, ethyl lactate, butyl acetate, isopropyl acetate, isobutyl acetate, isoamyl acetate, dichloroethane, dichloromethane, cyclohexane, heptane, toluene, and a mixture thereof.

11. The process according to claim 1, wherein the step of resolving the dl-threo-methylphenidate comprises resolving the dl-threo-methylphenidate with a derivative of a chiral amino acid;
 wherein the derivative of the chiral amino acid is a methanesulfonyl derivative, a para-toluenesulfonyl derivative, an acetyl derivative, a benzenesulfonyl derivative, a para-nitrobenzenesulfonyl derivative, a para-chlorobenzenesulfonyl derivative, or a combination thereof.

12. The process according to claim 1, wherein the step of resolving the dl-threo-methylphenidate comprises resolving the dl-threo-methylphenidate with a chiral amino acid or a derivative thereof;
 wherein the chiral amino acid or the derivative thereof is selected from the group consisting of L-methanesulfonyl valine, N-paratoluenesulfonyl valine, L-acetyl valine, leucine, isoleucine, L-phenyl alanine, methanesulfonyl aspartic acid, methanesulfonyl glutamic acid, benzenesulfonyl aspartic acid, benzenesulfonyl glutamic acid, paratoluenesulfonyl aspartic acid, N-paratoluenesulfonyl (tosyl) glutamic acid, paranitrobenzenesulfonyl aspartic acid, paranitrobenzenesulfonyl glutamic acid, parachlorobenzenesulfonyl aspartic acid, parachlorobenzenesulfonyl glutamic acid, and a combination thereof.

13. The process according to claim 1, wherein the dexmethylphenidate hydrochloride is produced with an optical purity of 97% to 99.9%.

14. The process according to claim 11, wherein the dexmethylphenidate hydrochloride is produced with an optical purity of 99% to 99.9%.

15. The process according to claim 12, wherein the dexmethylphenidate hydrochloride is produced with an optical purity of greater than 99.5% to 99.9%.

* * * * *